United States Patent [19]

Kurata et al.

[11] Patent Number: 4,814,462
[45] Date of Patent: Mar. 21, 1989

[54] POLYOXYALKYLENE CARBOZOLE ADDUCT

[75] Inventors: Naoji Kurata, Nishinomiya; Yoshio Sugita, Chiba; Keiji Kobayashi; Atsushi Kawano, both of Chiba, all of Japan

[73] Assignees: Nihon Joryu Kogyo Co., Ltd; Nippon Shokubai Kagaku Kogyo Co., Ltd., both of Osaka, Japan

[21] Appl. No.: 882,595

[22] Filed: Jul. 7, 1986

[30] Foreign Application Priority Data

Jul. 10, 1985 [JP] Japan ................................. 60-150001

[51] Int. Cl.$^4$ ............................................. C07D 209/86
[52] U.S. Cl. .................................................... 548/444
[58] Field of Search ......................................... 548/444

[56] References Cited

U.S. PATENT DOCUMENTS 3,894,041 7/1975 Otsuki et al. ........................ 548/444
4,342,688 8/1982 Tappe ................................. 548/444

FOREIGN PATENT DOCUMENTS 620733 5/1949 United Kingdom .

*Primary Examiner*—Robert W. Ramsuer
*Attorney, Agent, or Firm*—Omri M. Behr

[57] ABSTRACT

A polyoxyalkylene carbazole adduct represented by the following formula I:

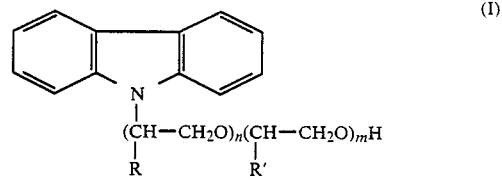

wherein R stands for at least one member selected from the group consisting of H, $CH_3$ and $C_6H_5$, R' for at least one member selected from the group consisting of $CH_3$, $C_6H_5$ and H, (providing that R' is at least one member selected from the group consisting of $CH_3$ and $C_6H_5$ when R is H, and R is at least one member selected from the group consisting of $CH_3$ and $C_6H_5$ when R' is H), n for an integer of the value of 0 to 500, m for an integer of the value of 0 to 500, and n+m for an integer of the value of 2 to 1000.

6 Claims, No Drawings

POLYOXYALKYLENE CARBOZOLE ADDUCT

BACKGROUND OF THE INVENTION

1. Field of the Invention:

This invention relates to novel polyoxyalkylene carbazole adducts and a method for the production thereof.

2. Description of the Prior Art:

Heretofore, the reaction of carbazole with an alkylene oxide, particularly ethylene oxide, has been effected by a procedure which comprises converting carbazole into an alkali metal salt of carbazole and allowing 1 mol of ethylene oxide to react upon the salt thereby effecting synthesis of N-hydroxyethylene carbazole, then dehydrating N-hydroxyethyl carbazole into vinyl carbazole and polymerizing vinyl carbazole thereby producing polyvinyl carbazole [U.S. Pat. No. 3,894,04, Japanese Patent Publication No. 49-9,468, C.A. 60:15837c (1964) and C.A. 63:565b (1965)].

We have made a study in search of means of effectively utilizing carbazole. They have consequently found that adducts obtained by adding alkylene oxides in an average of 2 to 1,000 mols to carbazole in a solvent, with a hydroxide or oxide of an alkali metal or an alkaline earth metal used as a catalyst, namely in an extremely small amount, especially adducts obtained similarly by adding ethylene oxide in 5 to 500 mols, can be effectively utilized as water-soluble cation-nonionic surfactants having low-foaming property, heat resistance, electroconductivity and a peculiar surface characteristic. This invention has been perfected as the result.

An object of this invention is to provide novel polyoxyalkylene carbazole adducts and a method for the production thereof.

SUMMARY OF THE INVENTION

The object described above is accomplished by polyoxyalkylene carbazole adducts represented by the formula I:

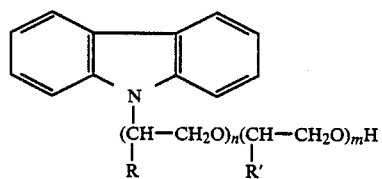

(I)

wherein R stands for at least one member selected from the group consisting of H, $CH_3$ and $C_6H_5$, R' for at least one member selected from the group consisting of $CH_3$, $C_6H_5$ and H, providing that R' is at least one member selected from the group consisting of $CH_3$ and $C_6H_5$ where R is H and R is at least one member selected from the group consisting of $CH_3$ and $C_6H_5$ where R' is H, n for an integer of a value of 0 to 500, and m for an integer of a value of 0 to 500, providing that n+m stand for an integer of the value of 2 to 1,000.

The aforementioned object is further accomplished by a method for the production of a polyoxyalkylene oxide adduct represented by the general formula I:

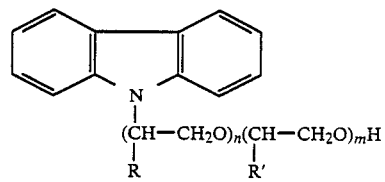

(I)

wherein R, R', n, and m have the same meanings as defined above, which method comprises subjecting carbazole to an addition reaction with an alkylene oxide in a solvent capable of dissolving carbazole and devoid of an active hydrogen in the presence of at least one catalyst selected from the group consisting of hydroxides and oxides of alkali metal and alkaline earth metals at a temperature in the range of 50° to 250° C. in the atmosphere of an inert gas containing substantially no molecular oxygen.

PREFERRED EMBODIMENT OF THE INVENTION

The polyoxyalkylene carbazole adducts contemplated by this invention are novel compounds and represented by the aforementioned formula I. In this formula, R is at least one member selected from the group consisting of H, $CH_3$ and $C_6H_5$ (phenyl), preferably H or $CH_3$ and R' at least one member selected from the group consisting of $CH_3$, $C_6H_5$, (phehyl) and H, preferably $CH_3$ or H. Further, R' is at least one member selected from the group consisting of $CH_3$ and $C_6H_5$, preferably $CH_3$, where R is H. By the same token, R is at least one member selected from the group consisting of $CH_3$ and $C_6H_5$, preferably $CH_3$, where R' is H. Then, n is an integer of the value of 0 to 500 and m an integer of the value of 0 to 500, and n+m an integer of the value of 2 to 1,000.

A polyoxyalkylene carbazole adduct of the foregoing description is obtained by dissolving carbazole in an organic solvent, adding to the resulting solution a catalytic amount of at least one member selected from the group consisting of hydroxides and oxides of alkali metals and alkaline earth metals, dehydrating the mixture in the atmosphere of an inert gas containing substantially no molecular oxygen, optionally by application of heat, vacuumization, or injection of a forced current of an inert gas, then subjecting the mixture to addition reaction of an inert gas, then subjecting the mixture to addition reaction of an alkylene oxide at a temperature in the range of 50° to 250° C. under atmospheric pressure or increased pressure and, after completion of the reaction, neutralizing the catalyst in the reaction mixture with an acid and optionally removing the neutalized catalyst from the reaction mixture, and subsequently recovering the organic solvent by means of distillation, for example.

The number of mols of the alkylene oxide so added is 2 to 1,000 on the average. The specific examples of the alkylene oxide are mainly ethylene oxide and propylene oxide. Occasionally, styrene oxide and butylene oxide are also included, which are added in the form of a block either before or after the addition of ethylene oxide. Adducts obtained by sole addition of propylene oxide or styrene oxide can be offered as non-aqueous products possessing a special surface characteristic.

The organic solvent to be used in the method of this invention is required to be incapable of reacting with the alkylene oxide, i.e. to be devoid of an active hydrogen, and capable of effectively dissolving carbazole. Any organic solvent, therefore, can be used so long as it fulfils this requirement. As typical examples of the organic solvent, aromatic hydrocarbons, aliphatic hydrocarbons, alicyclic hydrocarbons, and halides thereof, oxygen-containing compounds, and sulfur-containing compounds can be cited. Among other organic solvents enumerated above, aromatic hydrocarbons and aliphatic hydrocarbons, prove particularly desirable. Generally, aromatic hydrocarbons, particularly benzene, toluene, xylene, cumene, and pseudocumene can be easily used. Besides, paraffins having 6 to 20 atoms are generally used.

Typical examples of the catalyst used effectively in this invention are hydroxides and oxides of alkali metals and alkaline earth metals Among other catalysts enumerated above, hydroxides or oxides of alkali metals, especially hydroxides or oxides of potassium or sodium, are desirably used. The amount of the catalyst so used is in the range of 0.001 to 10% by weight, preferably 0.01 to 1% by weight, based on the total weight of carbazole as the raw material and ethylene oxide to be added.

The reaction temperature is in the range of 50° to 250° C., preferably 80° to 200° C. This reaction is carried out in a system thoroughly deprived of molecular oxygen. From the standpoint of safety, it is advantageous to perform this reaction in the presence of such an inert gas as nitrogen, helium, argon, methane, or propane, preferably nitrogen. Generally, this reaction is carried out under 1 to 20 kg/cm$^2$, preferably 2 to 10 kg/cm$_2$, or under an increased pressure. The carbazole solution is desired, before the alkylene oxide addition reaction and after the addition of the catalyst, to be subjected to a dehydration treatment at a temperature in the range of 100° to 200° C. under normal pressure or an decreased pressure in the presence of an inert gas or under continuous introduction of an inert gas.

After completion of the reaction, the solvent is recovered when necessary from the reaction mixture. This recovery is effected particularly desirably by distillation. Either before or after the recovery of the solvent, the catalyst used in the reaction mixture may be neutralized with an organic acid or a mineral acid and optionally removed from the reaction mixture by means of filtration or adsorption.

Now, the function of the polyoxyalkylene carbazole adduct of this invention and uses found for the adduct will be described below. The surfactants in accordance with the present invention have low-foaming property, heat resistance and electroconductivity.

When ethylene oxide is selected as the alkylene oxide and when the number of mols of ethylene oxide is in the range of 5 to 20, particularly 6 to 15, the produced adduct is used as an ordinarly water-soluble surfactant, specifically as a detergent, a penetrant, an emulsifier, a solubilizer, a dyeing assistant agent, and an antistatic agent which invariably feature excellence in surface tension lowering capacity and penetrating power. Similarly when the number of mols increases to 20 to 1,000, the produced adduct is used mainly as a dispersant or dispersion stabilizer for dispersion and stabilization of pigments, dyes, and fine solid particles (coal, tar pitch, and cement). When the number of mols is 2 to 15, the produced adduct is used in its unmodified form or esterified form as an antistatic agent or an electric property improver in various resins. When propylene oxide or styrene oxide is further added to the polyethylene oxide adduct, the produced composite adduct of a water-soluble grade serves as a surfactant of low-foaming property and the composite adduct of a water-insoluble grade often contributes to improving the solubility in oil and the compatibility with resin. When the alkylene oxide to be added first happens to be propylene oxide or styrene oxide, the produced adducts are useful as water-insoluble, i.e. oil-soluble antistatic agents and electric property improvers. When ethylene oxide is subsequently added to these adducts, the resultant composite adducts are useful as water-soluble surfactants adn, because of notable growth of oleophilic groups, serve as excellent surfactants for certain applications. They also show a decrease of C.M.C.

In any of the cases mentioned above, when the terminal hydroxyl group is sulfonated into a corresponding sulfuric ester salt, the adduct is converted into an anionic surfactant. There is consquently obtained an amphoteric surfactant possesing nonionicity and exhibiting a characteristic behavior.

Now, the present invention will be described below with reference to working examples. It should be noted, however, that this invention is not limited to these working examples.

EXAMPLE 1

In an autoclave made of stainless steel, 83.6 g (0.5 mol) of carbazole of purity of 99% by weight, 0.95 g of potassium hydroxide, and 334.4 g of xylene were placed and, with the entrapped air displaced with nitrogen gas to an initial pressure of 1 kg/cm$^2$, heated to 147° C. To the resulting reaction system, ethylene oxide was introduced for 2.5 hours to effect addition of 154.2 g (3.5 mols) of ethylene oxide. In this while, the reaction temperature was kept in the range of 145° to 150° C. The resulting reaction mixture was left aging for one hour and then left cooling. The reaction mixture was neutralized with acetic acid to pH 6.5. It was then blown with nitrogen at 120° under 20 mmHg for recovery of xylene. (Theoretical value for 7 mols, OH value=118.1)

The liquid carbazole-ethylene oxide adduct obtained as described above was found to possess a hydroxyl value of 119, indicating that the number of mols of ethylene oxide added was 6.9 on the average.

EXAMPLE 2

In an autoclave made of stainless steel, 83.6 g (0.5 mol) of carbazole having a purity of 99% by weight, 0.95 g of potassium hydroxide, and 334.4 g of xylene were placed and, with the trapped air displaced with nitrogen gas to an initial pressure of 1 kg/cm$^2$, heated to 140° C. To the resulting reaction system, propylene oxide was introduced for 3.5 hours to effect addition of 208.8 g (3.6 mols) of propylene oxide. In this while, the reaction temperature was kept in the range of 140° to 145° C. The reaction mixture was left aging for 1.5 hours and then left cooling. It was neutralized with phosphoric acid to pH 6.0. It was then blown with nitrogen at 120° C. under 20 mmHg for recovery of xylene.

The carbazole-propylene oxide adduct obtained as described above was found to possess a hydroxyl value of 98.9, indicating that the number of mols of propylene oxide added was 6.9 on the average.

EXAMPLE 3

In an autoclave made of stainless steel, 83.6 g (0.5 mol) of carbazole having a purity of 99% by weight, 500 g of xylene, and 0.95 g of potassium hydroxide were placed and, with the entrapped air displaced with nitrogen gas to an initial pressure of 1 kg/cm², heated to 147° C. To the resulting reaction system, ethylene oxide was introduced for 2.5 hours to effect addition of 154.2 g (3.5 mols) of ethylene oxide. In this while, the reaction temperature was kept in the range of 145° to 150° C. The reaction mixture was left aging for one hour. Then propylene oxide was introduced to the reaction system for two hours to effect addition of 104.4 g (1.8 mols) of propylene oxide. In this while, the reaction temperature was kept in the range of 145° to 140° C. The reaction mixture was left aging for one hour and then left cooling. It was neutralized with phosphoric acid to pH 6.0. Then, it was blown with nitrogen at 120° C. under 20 mmHg for recovery of xylene.

The carbazole ethylene oxide-propylene oxide adduct obtained as described above was found to have a hydroxyl value of 83.3, indicating that 6.9 mols of ethylene oxide and 3.5 mols of propylene oxide were added on the average.

EXAMPLE 4

In an autoclave made of stainless steel, 83.6 g (0.5 mol) of carbazole having a purity of 99% by weight, 500 g of xylene, and 0.95 g of potassium hydroxide were placed and, with the trapped air displaced with nitrogen gas to an initial pressure of 1 kg/cm², heated to 140° C. To the resulting reaction system, propylene oxide was introduced for two hours to effect addition of 104.4 g (1.8 mols) of propylene oxide. In this while, the reaction temperature was kept in the range of 140° to 145° C. The reaction mixture was left aging for 1.5 hours. Then ethylene oxide was introduced to the reaction system for 2.5 hours to effect addition of 154.2 g (3.5 mols) of ethylene oxide. In this while, the reaction temperature was kept in the range of 145° to 150° C. The reaction mixture was left aging for one hour and then left cooling. It was then neutralized with lactic acid to pH 6.5. It was then blown with nitrogen at 120° C. under 20 mmHg for recovery of xylene.

The carbazole propylene oxide-ethylene oxide adduct obtained as described above was found to have a hydroxyl value of 83.3, indicating that 3.5 mols of propylene oxide and 6.8 mols of ethylene oxide were added on the average.

EXAMPLE 5

In an autoclave made of stainless steel, 83.6 g (0.5 mol) of carbazole having a purity of 99% by weight, 800 g of a straight chain paraffin having 12 to 14 carbon atoms and an average of 13 carbon atoms, and 3.0 g of potassium hydroxide were blown with nitrogen gas at 160° C. under 300 mmHg two hours to effect dehydration. The reaction mixture was pressed with nitrogen to 5 kg/cm² and heated to 150° C. To the resulting reaction system, 1147 g (26 mols) of ethylene oxide was added over 5 hours. In this while, the reaction temperature was kept in the range of 145° to 155° C. It was left aging for 1.5 hours and then left cooling. It was neturalized with acetic acid to pH 6.5. Then, it was blown with nitrogen under 10 mmHg for recovery of the straight-chain paraffin.

The carbazole ethylene oxide adduct obtained as described above was found to have a hydroxyl value of 24.8, indicating that the number of mols of ethylene oxide added was 49.5 on the average.

Properties of polyoxyalkylene carbazole adducts in accordance with the present invention are shown in Table 1.

Decreasing rates by thermogravimetric analysis in air of polyoxyalkylene carbazole adducts in accordance with the present invention and 3 mols of ethylene oxide adduct of straight chain secondary alcohol having 12 to 14 carbon atoms are shown in Table 2.

Antistactic effect of polyoxyalkylene carbazole adducts are shown in Table 3.

TABLE 1

| Polyoxyalkylene carbazole adducts | | | Viscosity (cP) 25° C. | Viscosity (cP) 50° C. | Viscosity (cP) 80° C. | Cloud point 1% aq. soln. (°C.) | Surface tension 0.1% aq. soln. (dyne/cm²) 25° C. | Foaming force 0.1% aq. soln. (mm) 0 min. | Foaming force 0.1% aq. soln. (mm) 2 min. | Foaming force 0.1% aq. soln. (mm) 5 min. | Penetrating force aq. soln. (wool) (sec) 0.05% | Penetrating force aq. soln. (wool) (sec) 0.1% | Penetrating force aq. soln. (wool) (sec) 0.2% | Pour point (°C.) |
|---|---|---|---|---|---|---|---|---|---|---|---|---|---|---|
| | | added EO mols | | | | | | | | | | | | |
| EO adduct of carbazole | | 3 | 3,500 | 310 | 42 | water insol. | — | — | — | — | — | — | — | −8 |
| | | 7 | 820 | 170 | 37 | 25 | 43 | 12 | 7 | 6 | 106 | 17 | 7 | 8 |
| | | 10 | 710 | 150 | 37 | 57 | 44 | 53 | 15 | 13 | 161 | 30 | 11 | 9 |
| | | 20 | — | 170 | 58 | 92 | 50 | 53 | 14 | 5 | 300< | 300< | 300< | 26 |
| | | 50 | — | 310 | 130 | 100< | 53 | 58 | 4 | 3 | 300< | 300< | 300< | 43 |
| | | 100 | — | — | 270 | 100< | 56 | 32 | 11 | 9 | 300< | 300< | 300< | 52 |
| | | 300 | — | — | 1,100 | 100< | 60 | 22 | 3 | 2 | 300< | 300< | 300< | 54 |
| | added EO mols | added PO mols | | | | | | | | | | | | |
| EO-PO adduct of carbazole obtained by adding EO and then adding PO. | 5 | 3 | 690 | 130 | 35 | water insol. | — | — | — | — | — | — | — | −10> |
| | 7 | 3 | 620 | 110 | 35 | 27 | 42 | 3 | 0 | 0 | 89 | 20 | 8 | −10> |
| | 7 | 4.5 | 590 | 100 | 33 | 24 | 42 | 3 | 0 | 0 | 47 | 15 | 8 | −10> |
| | 7 | 6 | 400 | 120 | 34 | 20 | 40 | 3 | 0 | 0 | 28 | 12 | 7 | −10> |
| | 7 | 10 | 420 | 110 | 36 | 17 | — | 3 | 0 | 0 | 25 | 11 | 6 | −10> |
| | 10 | 3 | 540 | 130 | 43 | 39 | 45 | 3 | 0 | 0 | 122 | 39 | 15 | −10> |
| | 10 | 4.5 | 590 | 140 | 45 | 34 | 43 | 5 | 0 | 0 | 97 | 30 | 11 | −10> |
| | 10 | 6 | 530 | 140 | 44 | 30 | 41 | 4 | 0 | 0 | 58 | 20 | 9 | −10> |
| | added PO mols | added EO mols | | | | | | | | | | | | |
| PO-EO adduct of carbazole | 3 | 3 | 1,600 | 150 | 38 | water insol. | — | — | — | — | — | — | — | −10> |
| | 3 | 7 | 1,800 | 150 | 41 | 42 | 40 | 18 | 6 | 5 | 42 | 14 | 7 | 15 |

TABLE 1-continued

| Polyoxyalkylene carbazole adducts | | Viscosity (cP) 25° C. | Viscosity (cP) 50° C. | Viscosity (cP) 80° C. | Cloud point 1% aq. soln. (°C.) | Surface tension 0.1% aq. soln. (dyne/cm²) 25° C. | Foaming force 0.1% aq. soln. (mm) 0 min. | Foaming force 0.1% aq. soln. (mm) 2 min. | Foaming force 0.1% aq. soln. (mm) 5 min. | Penetrating force aq. soln. (wool) (sec) 0.05% | Penetrating force aq. soln. (wool) (sec) 0.1% | Penetrating force aq. soln. (wool) (sec) 0.2% | Pour point (°C.) |
|---|---|---|---|---|---|---|---|---|---|---|---|---|---|
| obtained by adding PO 5 and then adding EO. | 3 10 | 1,200 | 130 | 49 | 58 | 40 | 16 | 5 | 3 | 69 | 22 | 8 | 18 |
| | 3 930 | 140 | 36 | water insol. | — | — | — | — | — | — | — | −10> | |
| | 5 7 | 2,000 | 120 | 42 | 38 | 38 | 13 | 0 | 0 | 27 | 12 | 5 | 7 |
| | 5 10 | 830 | 140 | 55 | 56 | 38 | 22 | 4 | 2 | 41 | 18 | 10 | 16 |
| | 7 3 | 680 | 120 | 33 | water insol. | — | — | — | — | — | — | — | −10> |
| | 7 7 | 520 | 110 | 41 | 37 | 37 | 16 | 0 | 0 | 30 | 18 | 5 | −5 |
| | 7 10 | 540 | 140 | 46 | 51 | 37 | 17 | 0 | 0 | 30 | 14 | 5 | 13 |

EO: ethylene oxide
PO: propylene oxide
Measuring method:
Viscosity: B typ rotary viscosimeter
Foaming force: JISK-3362(1978) based on (Rosmiles method)
Penetrating force: JISK-3362(1955) based on (wool)

TABLE 2

| Temperature (°C.) | Decreasing ratio (%) 0 | 100 | 150 | 200 | 250 | 300 | 350 | 400 | 500 |
|---|---|---|---|---|---|---|---|---|---|
| 3 mols ethylene oxide of carbazole | 0 | 0.1 | 0.2 | 0.5 | 1.2 | 5.8 | 35.8 | 90.9 | 94.7 |
| 3 mols ethylene oxide adduct of straight chain secondary alcohol having 12–14 carbon atoms | 0 | 0.4 | 1.2 | 2.3 | 15.6 | 73.9 | 94.6 | 95.8 | 97.8 |

Thermogravimetric Analysis(TGA)
Sample: 17 mg
Prog. speed: 10° C./min.
Air flow: 30 ml/min.
Temp. range: 25 mv

TABLE 3

Frictional dielectric strength in nylon cloth

| Sample | Concentration of aq. soln. (%) | Dielectric strength (kV) |
|---|---|---|
| Water (no surfactant) | 0 | min. 10 |
| 3 mols of EO adduct of carbazole | 1.0 | 0 |
| 7 mols of EO adduct of carbazole | 1.0 | 0 |
| 10 mols of EO adduct of carbazole | 1.0 | 4 |
| 20 mols of EO adduct of carbazole | 1.0 | 2 |
| 50 mols of EO adduct of carbazole | 1.0 | 7 |
| 100 mols of EO adduct of carbazole | 1.0 | 5 |
| 300 mols of EO adduct of carbazole | 1.0 | 5 |
| 7 mols of EO and 3 mols of PO adduct of carbazole | 1.0 | 4 |
| 10 mols of EO and 3 mols of PO adduct of carbazole | 1.0 | 3 |
| 7 mols of EO and 10 mols of PO adduct of carbazole | 1.0 | 2 |

Measuring method: Nylon cloth having 10 cm × 10 cm size is depasted and degreased with carbon tetrachloride, dipped in 60 ml of a sample solution at 45° C., and then dried to obtain a test cloth. The test cloth is frictioned by a plastic rod to generate electrostatics and the cloth is subjected to dielectric test by using a electrostatic checker (manufactured by Nippon Kayaku Kabushiki Kaisha).

What is claimed is:

1. A polyoxyalkylene carbazole adduct represented by the following formula I:

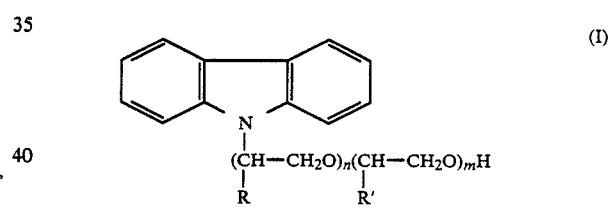

wherein R stands for at least one member selected from the group consisting of H, $CH_3$ and $C_6H_5$, R' for at least one member selected from the group consisting of $CH_3$, $C_6H_5$ and H, (providing that R' is at least one member selected from the group consisting of $CH_3$ and $C_6H_5$ when R is H, and R is at least one member selected from the group consisting of $CH_3$ and $C_6H_5$ wherein R' is H), n is an integer of the value of 6 to 500, m is an integer of the value of 0 to 500, and n+m is an intger of the value of 6 to 1000.

2. An adduct according to claim 1, wherein R is $CH_3$ and R' is $CH_3$.

3. An adduct according to claim 1, wherein R is H, n is 6 to 500, and m is 0.

4. An adduct according to claim 1, wherein R is $CH_3$, n is 6 to 500, and m is 0.

5. An adduct according to claim 1, wherein R is H and R' is $CH_3$ and m is other than 0.

6. An adduct according to claim 1, wherein R is $CH_3$ and R' is H and m is other than 0.

* * * * *